(12) United States Patent
Vallone

(10) Patent No.: US 8,292,832 B2
(45) Date of Patent: Oct. 23, 2012

(54) EVENT-BASED HEALTH ACTIVITY TRACKING WITH ICON-BASED USER INTERFACE

(76) Inventor: Anthony Vallone, North Canton, OH (US)

( * ) Notice: Subject to any disclaimer, the term of this patent is extended or adjusted under 35 U.S.C. 154(b) by 369 days.

(21) Appl. No.: 12/509,978

(22) Filed: Jul. 27, 2009

(65) Prior Publication Data

US 2011/0021952 A1 Jan. 27, 2011

(51) Int. Cl.
*A61B 5/11* (2006.01)
(52) U.S. Cl. ............... 600/595; 705/2; 482/1; 482/2; 128/920; 128/923; 715/763; 600/300; 600/301
(58) Field of Classification Search ........... 128/920–925
See application file for complete search history.

(56) References Cited

U.S. PATENT DOCUMENTS

| | | | |
|---|---|---|---|
| 4,839,822 A * | 6/1989 | Dormond et al. | 706/45 |
| 7,041,032 B1 * | 5/2006 | Calvano | 482/4 |
| 7,231,611 B2 * | 6/2007 | Kumhyr et al. | 715/837 |
| 2005/0288154 A1 * | 12/2005 | Lee et al. | 482/3 |
| 2007/0136093 A1 * | 6/2007 | Rankin et al. | 705/2 |
| 2008/0203144 A1 * | 8/2008 | Kim | 235/105 |

* cited by examiner

*Primary Examiner* — Sam Yao
*Assistant Examiner* — Marie Archer
(74) *Attorney, Agent, or Firm* — Cooper Legal Group LLC

(57) ABSTRACT

A health activity plan may be prescribed for an individual comprising a set of health activity instances (e.g., physical therapy exercises, an exercise regimen, or a wound management program.) The performed health activity instances of the individual may be tracked by a device, and may be presented to a user of the device in correlation with the health activity plan (e.g., to demonstrate compliance of the individual with the health activity plan.) The health activity information may be presented using a set of icons that depict the health activity information, which may improve an easier understanding and a more consistent communication of health activity information among the individual and healthcare providers.

18 Claims, 7 Drawing Sheets

EVENT-BASED HEALTH ACTIVITY TRACKING WITH ICON-BASED USER INTERFACE

BACKGROUND

Within the field of computing, many scenarios involve a tracking of health activities of an individual. As a first example, a user may choose to follow a particular health regimen, such as an exercise plan or a dietary supplement plan, and may use a calendar or journal to record a set of activities that the individual has performed in accordance with this regimen. As a second example, a physician may prescribe a set of health activities, e.g., a set of physical therapy exercises to be performed by an individual, and a second healthcare provider of the individual, such as a physical therapist, may observe the performance of the exercises by the individual and record such observations in a database (e.g., as part of the individual's electronic medical record.) As a third example, a device provided to an individual may be configured to record a set of health-related activities performed by the individual, such as the changing of a bandage or a self-performed examination of a health condition. In these and other scenarios, one or more computer systems may be used to detect, record, and report the individual's performance of the health activities.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

Within the scenarios described herein and similar scenarios, some disadvantages may arise in particular configurations of computer systems used to track the performance of health activities of an individual. As one such drawback, the computer system may not be programmed with the regimen to which the performed activities relate. As a first example, the individual may record exercise activities in an electronic calendar, but no indication may be computable as to the conformity of the recorded activities with the anticipated exercise regimen of the individual. As a second example, a healthcare provider may describe a prescribed health regimen for the individual in one form (e.g., in an electronic medical record), but this entry may be described in natural language, prose, or another form that is not easily correlated in an automated manner with records of the performance of these activities by the individual, thereby necessitating the involvement of a human to evaluate the disjointed records to determine the conformity of the individual with the health regimen. As a second such drawback, the computer system may not be configured to communicate with the individual (as well as one or more healthcare providers involved in the care of the individual) in a convenient manner. For example, the records of the individual's performance of the activities might be displayed as a set of recorded metrics or prosaic descriptions that may be difficult for some users of the computer system to understand. Additionally, it may be difficult to communicate such information among a set of users, such as healthcare providers and the individual, if one or more users speak different languages or have low rates of literacy or understanding of technical terminology.

Presented herein is an alternative technique for configuring an activity tracking system to detect, record, and report the health activities of an individual that may present particular advantages with respect to conventional systems. An activity tracking system may be configured to store in memory a health activity plan, comprising a set of prescribed health activity instances of one or more health activity types that are to be performed by the individual. The activity tracking system may then be configured to receive notifications of a performance of a health activity instance of the individual, and to store in memory a record indicating the performance of the health activity instance of a health activity type. Moreover, when the activity tracking system is requested to present a report of the health activities of the individual, the activity tracking system may present to the user the set of health activity instances in at least two distinctive ways. As a first example, the health activity instances may be correlated with the prescribed health activity instances to illustrate the conformity of the individual's activities with the prescribed activity plan. As a second example, the performed health activity instances may be presented as icons selected from an icon set, where such icons depicting the performed health activity instances of particular health activity types. This presentation may promote the communication of health activity information in a more readily and commonly understandable manner, regardless of the language proficiencies or language differences of the various users of the activity tracking system. Moreover, the icon set may be standardized across a set of health-related system (e.g., the individual's electronic medical record, medication reminder devices, and service tracking devices provided to healthcare providers of the individual) to present a more consistent communications mechanism that may facilitate cognition, reduce errors, and promote the quality of healthcare for the individual.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
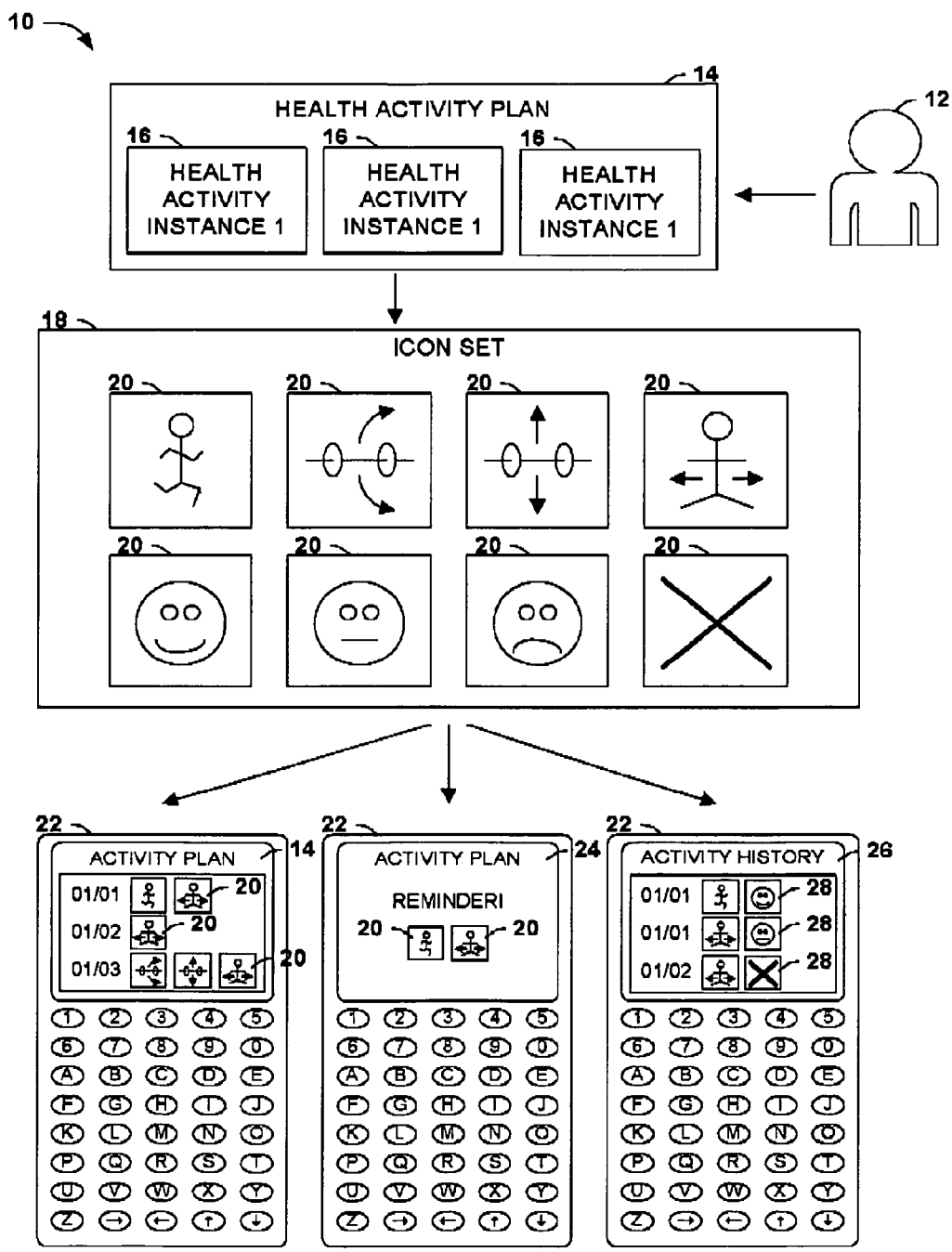
FIG. 1 is an illustration of an exemplary scenario featuring an illustration of health activities using icons.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

The present disclosure relates to the recording and presentation of health activities that may be performed by an individual, such as stretching exercises comprising a physical therapy regimen, workout activities in an exercise routine or weight-training program, the changing of a bandage or wound dressing, or a self-performed examination. In these and other scenarios, a health activity plan may be prescribed for or adopted by an individual, and the individual may be committed to performing such activities. The health activity plan may comprise a set of prescribed health activity types (e.g., one or more particular physical therapy exercises), each of which is to be performed as one or more health activity instances, e.g., as occasions on which such health activity types are to be performed.

In these scenarios, it may be helpful to facilitate the individual in performing and tracking the performance of the health activities. As a first example, it may be helpful to display the health activity plan in a convenient manner, such as a calendar format, in order to assist the individual in planning to perform the health activity instances. As a second example, reminders may be rendered to prompt the individual in performing a prescribed health activity instance in order to promote compliance. As a third example, annotations of the health activity to be performed, such as textual or spoken explanations of the health activity type or illustrative diagrams or video, may be presented to the individual to facilitate the correct and complete performance of the health activities. As a fourth example, various details of the performance of the health activity may be recorded, such as detected indications of the correct performance of the health activity and annotations by the individual describing the health activity instance. As a fifth example, the historic record of the performance of the health activities may be presented and analyzed in various ways, such as to demonstrate the progress of the individual in a physical therapy regimen or exercise routine or to measure the compliance of the individual with the health activity plan.

Many techniques may be devised to promote and track the performance by the individual of the health activities comprising the health activity plan. However, one significant challenge in many such techniques is the convenient and consistent presentation of information. As a first example, the individual may have difficulty understanding a textual description of the health activity plan, e.g., textual names of activities prescribed by a healthcare provider, and may perform such activities in ways or instances different than prescribed. As a second example, the recordings of such information by an individual or device might be difficult to interpret by a healthcare provider, e.g., if inconsistent terminology is used or if information is presented as numeric data that is not easily evaluated by a healthcare provider. As a third example, the healthcare provider(s) and the individual may communicate in different languages, at different levels of technical complexity, or with different terminology drawn from various fields of health sciences, and the language differences may contribute to a divergence of the individual from the health activity plan or an incorrect evaluation of the record of the performed health activity instances. As a fourth example, different devices or systems may present information in different formats or with different communicative interfaces, and even if such formats and interfaces are cognizable and convenient, the differences may lead to confusion, misunderstandings, inconsistent record keeping, or avoidable complexity in the presentation of the health activity information to the individual and healthcare providers. These difficulties may be exacerbated with a larger set of concurrently or sequentially involved healthcare providers, with additional or dynamic health-related information systems, and with the complexity of the health activity plan prescribed for the individual.

One technique for alleviating these complications involves a consistent presentation of health activity information to the individual. As one example, health information system may incorporate and utilize a set of icons that, when used in isolation or in combination, depict some concepts relating to the health activity plan, such as the health activity types and various descriptors of performed health activities (e.g., the proficiency with which a particular health activity was performed during a particular health activity instance.) The health information system may communicate with the individual and healthcare providers through the presentation of such icons, which may promote the consistent understanding of the health activity plan and the record of the performed health activity instances. Moreover, a standardized icon set may be devised and incorporated by a large and disparate set of such health information systems. This adoption may promote a consistent presentation of the health activity information in a variety of contexts related to respective health information systems, and may promote the compliance of the individual with the health activity plan.

FIG. 1 presents an exemplary illustration 10 of the use of an icon set 18 in the conveyance of health activity information. A health activity plan 14, comprising a series of health activity instances 16, may be formulated for an individual 12. In order to facilitate the compliance of the individual 12 with the health activity plan 14, a device 22 may be provided into which the health activity plan 14 may be programmed. The device 18 may also be configured to store an icon set 18, comprising a set of icons 20 that depict different health activity types (e.g., running, a weight-curling exercise, a weight-pressing exercise, and a stretching exercise.) The icons set 18 may also comprise other types of icons 20, e.g., icons representing indicators of the proficiency with which a health activity instance was performed by the individual 12 (such as "well," "OK," "poorly," and "not performed," as illustrated in FIG. 1.) On such a device 22, the health activity plan 14 may be illustrated to the individual 12 (and any other user of the device 22, such as a healthcare provider) through the presentation of corresponding icons 20. As a first example, the device 22 may present to a user of the device 22 the set of prescribed health activities comprising the health activity plan 14, e.g., as a set of dates with a presentation of icons representing the health activities 16 to be performed on the respective dates. (More specifically, the icons 20 may represent health activity types—e.g., a particular type of exercise or stretching—and for respective health activities 16 prescribed for respective dates, an icon 20 may be selected and presented that depicts the health activity type of the health activity 16.) As a second example, when a health activity instance is due to be performed by the individual 12, the device 22 may present a reminder 24 indicating the health activity types to be performed for the health activity instance. As a third example, the device 22 may, upon receiving a request of a user of the device 22, present a health activity history 26 by displaying icons 20 representing the health activity instances 16 that have been performed, correlated to the prescribed health activity instances 16. For example, for respective prescribed health activity instances 16, an icon 20 representing the health activity instance type may be displayed, along with an indicator 28 of the proficiency with which the individual 12 performed the health activity instance 16. Many other renderings of the health activity plan 14 and health activity instances 16 may be devised and presented on the device 22 through the use of icons 20, and such presentations may be advantageous, e.g., for communicating the concepts of the health activity plan 14 to the individual 12 (or other users) in a clear, consistent, and language-neutral manner.

Figure 2:
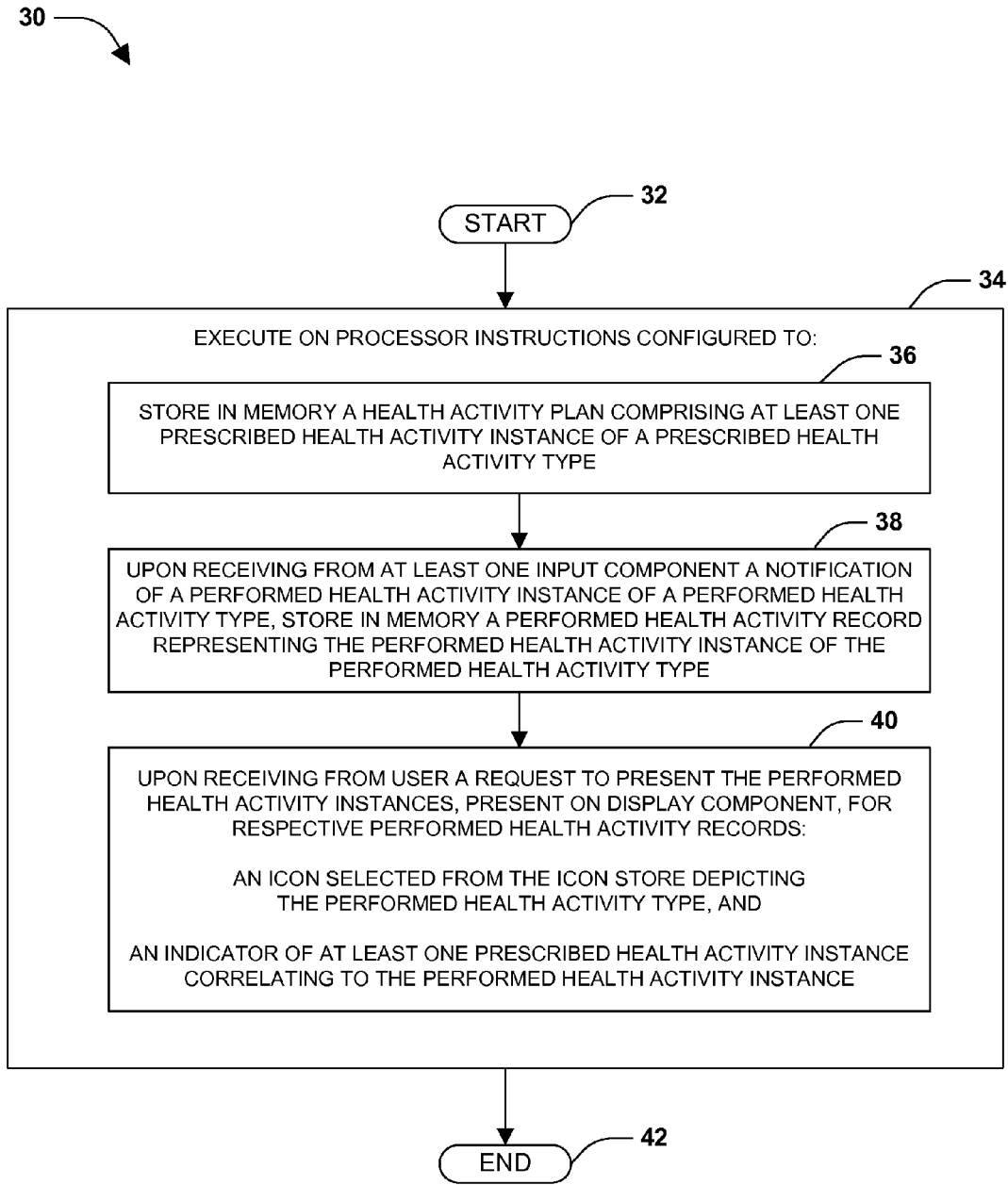
FIG. 2 is a flow chart illustrating an exemplary method of tracking health activities prescribed for and performed by an individual.

FIG. 2 presents a first embodiment of these techniques, illustrated as an exemplary method 30 of tracking health activities prescribed for and performed by an individual 12. The exemplary method 30 begins at 32 and involves executing 34 instructions on a processor 58 configured to operate according to the techniques discussed herein. The instructions may be configured to execute on a device having a memory, at least one input component, at least one display, and an icon store configured to store health activity icons depicting health activity types. In this context, the instructions may be configured to store 36 in the memory a health activity plan comprising at least one prescribed health activity instance of a prescribed health activity. The instructions may also be configured to, upon receiving from at least one input component a notification of a performed health activity instance of a performed health activity type, store 38 in the memory a performed health activity record representing the performed health activity instance of the performed health activity type. Finally, the instructions may be configured to, upon receiving from the user a request to present the performed health activity instances, present 40 on the display component, for respective performed health activity records, an icon selected from the icon store depicting the performed health activity type, and an indicator of at least one prescribed health activity instance correlating to the performed health activity instance. Having achieved the presentation of the health activity instances of the individual correlated with the health activity plan, the exemplary method 30 ends at 42.

Figure 3:
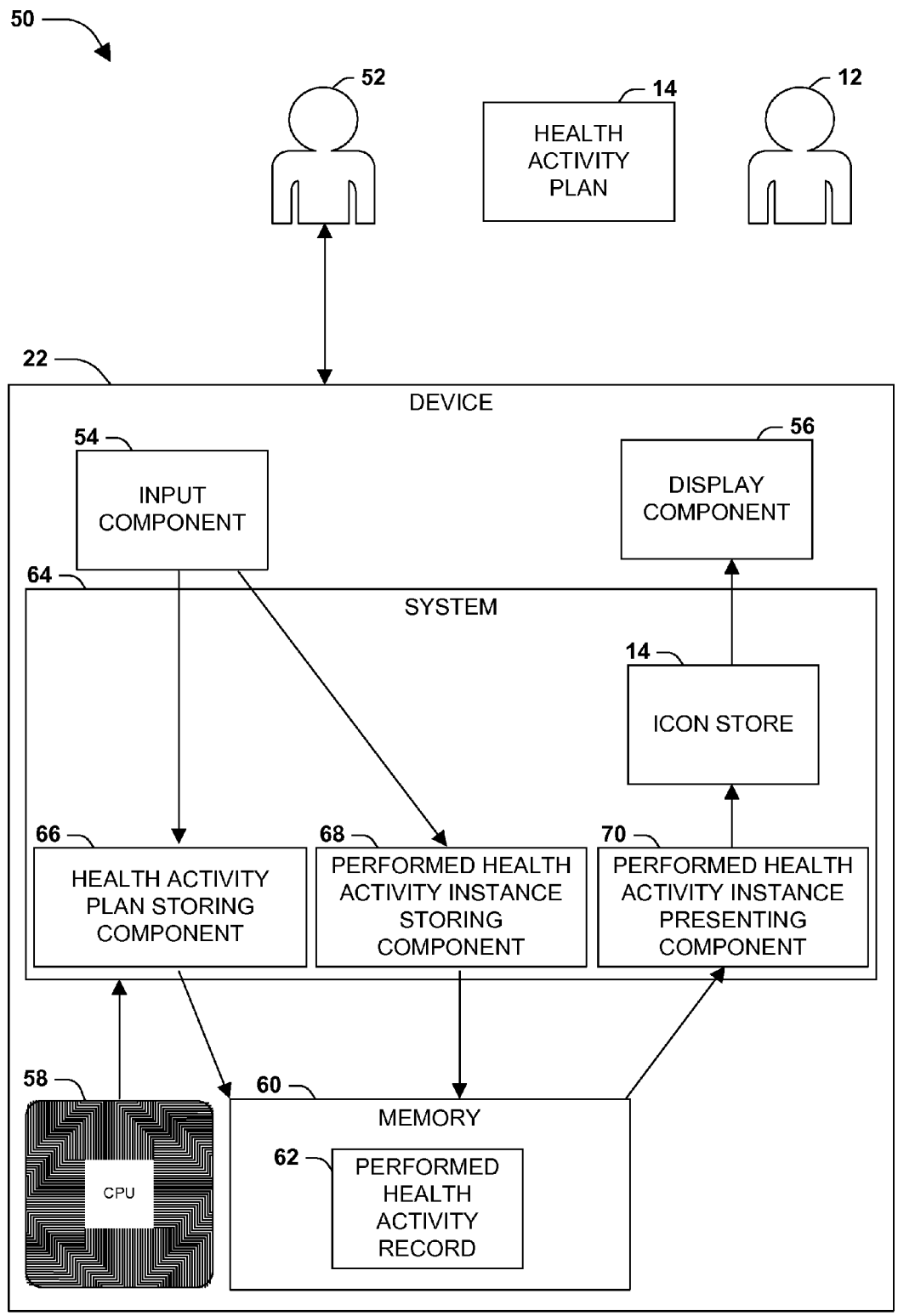
FIG. 3 is a component block diagram illustrating an exemplary system for tracking health activities prescribed for and performed by an individual.

FIG. 3 presents a second embodiment of these techniques, illustrated as an exemplary system 64 configured to track health activities prescribed for and performed by an individual 12. The exemplary system 64 may be implemented on a device 22 having at least one display component 56, at least one input component 54, a memory 60, and a processor 58, which may be operated by a user 52 (e.g., the individual 12 or a healthcare provider of the individual 12.) The exemplary system 64 may be implemented, e.g., as a set of software instructions configured to execute according to the techniques discussed herein. For example, the exemplary system 64 may comprise an icon store 14 configured to store health activity icons pictorially representing health activity types. The exemplary system 64 may also comprise a health activity plan storing component 66 configured to store in the memory a health activity plan 14 comprising at least one prescribed health activity instance of a prescribed health activity type. The exemplary system 64 may also comprise a performed health activity instance storing component 68 configured to, upon receiving from the input component 54 a notification of a performed health activity instance of a performed health activity type, store in the memory a performed health activity record 62 representing the performed health activity instance of the performed health activity type. Finally, the exemplary system 64 may comprise a performed health activity instance presenting component configured to, upon receiving from a user 52 of the device 22, a request to present the performed health activity instances, present on the display component 56, for respective performed health activity records 62, an icon 20 selected from the icon store 14 that depicts the performed health activity type, and an indicator of at least one prescribed health activity instance correlating to the performed health activity instance. The exemplary system 64 thereby achieves the tracking of the health activity plan 14 of the individual 12 and the presentation of the health activity plan 14 to the user 52.

The techniques discussed herein may be devised with variations in many aspects, and some variations may present additional advantages and/or reduce disadvantages with respect to other variations of these and other techniques. Moreover, some variations may be implemented in combination, and some combinations may feature additional advantages and/or reduced disadvantages through synergistic cooperation. The variations may be incorporated in various embodiments (e.g., the exemplary method #R of FIG. 2 and the exemplary system 64 of FIG. 3) to confer individual and/or synergistic advantages upon such embodiments.

A first aspect that may vary among embodiments of these techniques relates to the architecture of embodiments thereof. A first exemplary architecture is illustrated in FIG. 3 as an exemplary system 64, which may be implemented, e.g., as a set of instructions configured to, when executed on a processor 58, cause the processor 58 to perform the techniques discussed herein.

Figure 4:
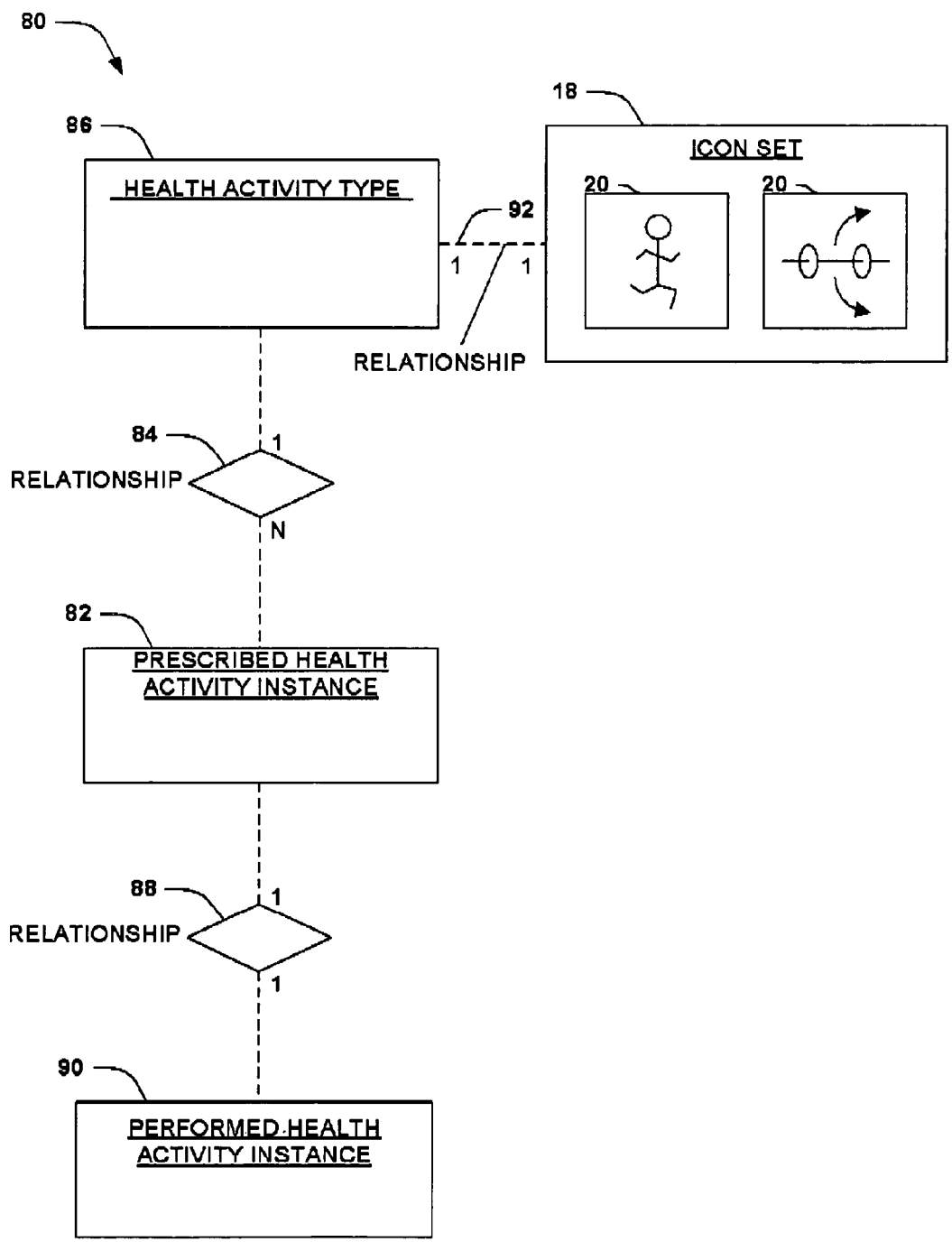
FIG. 4 is an Entity-Relationship Diagram (ERD) illustrating an exemplary organization of data comprising a device configured according to the techniques discussed herein.

FIG. 4 presents an exemplary organization of data stored by a device 22 to represent the health activity plan 14 and the health activity instances 16. This organization is illustrated as an Entity-Relationship Diagram (ERD) of a portion of a database that may be configured to store representations of the health activity plan 14 and health activity instances 16. The health activity plan 14 may be represented as a set of prescribed health activity instances 82, such as scheduled occasions on which particular exercises are to be performed. The prescribed health activity instances 82 may have a relationship 84 with a set of health activity types 86, which may represent, e.g., the different types of exercises and stretches that may be prescribed for the individual 12. The prescribed health activity instance 82 may also include other information, e.g., the date or time for which the health activity instance is scheduled, the difficulty of the prescribed health activity instance 82 (e.g., the amount of weight to use in an exercise or the degree of stretching to be achieved), and/or annotations about the prescribed health activity instance 82 generated by a healthcare provider. In this exemplary ERD, each prescribed health activity instance 82 may identify only one health activity type 86, but several health activity instances 82 (of different health activity types 86) may be scheduled for a particular day. The device 22 may also be configured to store a set of performed health activity instances 90 corresponding to the prescribed health activity instances 82 through a relationship 88. The performed health activity instances 90 may also contain additional information, e.g., the proficiency of the performed health activity instance 90 achieved by the individual 12 or an annotation about the performance of the performed health activity instance 90. Finally, the health activity types 86 may be correlated with icons 20 of the icon set 18 to present the health activity types 86 of the health activity instances 16 on the device 22. In this manner, records may be generated and stored to represent the health activity plan 14 of the individual 12.

Figure 5:
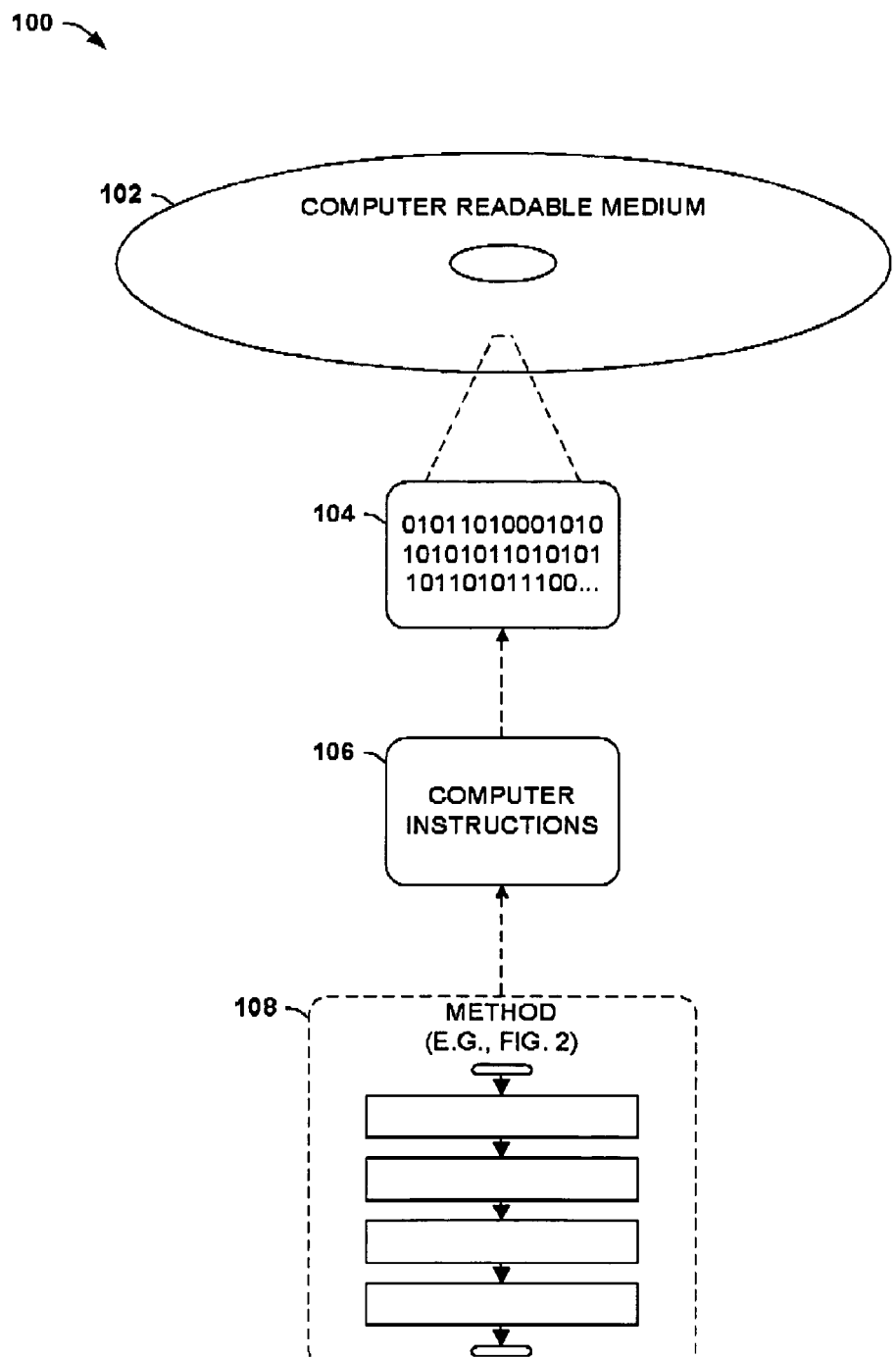
FIG. 5 is an illustration of an exemplary computer-readable medium comprising processor-executable instructions configured to embody one or more of the provisions set forth herein.

Still another architecture wherein these techniques may be implemented involves a computer-readable medium comprising processor-executable instructions configured to apply the techniques presented herein. An exemplary computer-readable medium that may be devised in these ways is illustrated in FIG. 5, wherein the implementation 100 comprises a computer-readable medium 102 (e.g., a CD-R, DVD-R, or a platter of a hard disk drive), on which is encoded computer-readable data 104. This computer-readable data 104 in turn comprises a set of computer instructions 106 configured to operate according to the principles set forth herein. In one such embodiment, the processor-executable instructions 106 may be configured to perform a method of tracking health activities prescribed for and performed by an individual, such as the exemplary method 30 of FIG. 2. In another such embodiment, the processor-executable instructions 106 may be configured to implement a system for tracking health activities prescribed for and performed by an individual, such as the exemplary system 64 of FIG. 3. Many such architectures may be devised by those of ordinary skill in the art that are configured to operate in accordance with the techniques presented herein.

A second aspect that may vary among embodiments of these techniques relates to the manner of defining the health activity plan 14 of the individual 12. As a first variation, the health activity plan 14 may be represented as a data set that is loaded onto the device 22 through a communications component, such as a network adapter that is capable of receiving a transmission of the data set from another device or computer, or a memory reader that is capable of reading a removable media item (e.g., a flash memory device) onto which the data set is loaded. As a second variation, the health activity plan 14 may be generated on the device 22 by a user 52 of the device 22 (such as the individual 12 or a healthcare provider of the individual 12.) In one such embodiment, the instructions comprising an embodiment of these techniques may be configured to receive the health activity plan 22 by displaying for the user 52 icons 20 selected from the icon store 14 and depicting health activity types that may be prescribed for the individual 12. The health activity plan may then be stored by, upon receiving a selection by the user 52 of at least one icon 20 (e.g., as detected by the input component 54), storing in the memory 60 a prescribed health activity instance 82 of the health activity type 86 represented by the selected icon 20. Those of ordinary skill in the art may devise many techniques for storing the health activity plan in the memory 60 while implementing the techniques discussed herein.

A third aspect that may vary among embodiments of these techniques relates to the receiving of notifications that the individual 12 has performed a health activity instance. As a first variation, the input component 54 may be configured to receive the notification of the performed health activity instance from the user 52 (e.g., from the individual 12 or from a healthcare provider of the individual 12 who observes and can report on the performance of the health activity, such as a physical therapist.) In one such embodiment, an input component 54 may be configured to receive the notification of the performed health activity instance by displaying for the user 52 (e.g., on the display component 56) at least one icon 20 selected from the icon store and depicting the health activities that may be performed by the individual 12, and by receiving from the user 52 a selection of at least one icon 20. Alternatively or additionally, the input component 54 may be configured to receive the notification from at least one detector configured to detect performances of the prescribed health activity instances by the individual 12. For example, a running shoe may be configured to detect the performance of a running exercise, and to report the detected performance to the exemplary system 64 of FIG. 3 for recording in the memory 60 as a performed health activity instance. Alternatively or additionally, other types of information may be received and included in the performed health activity record 62. For example, the input component 54 may receive (e.g., from the user 52 or a detector) at least one performed health activity instance descriptor that described the performed health activity instance, such as the performed health activity type, the time of the performed health activity instance, a proficiency of the performed health activity instance, an at least partial recording of the performed health activity instance, and/or an annotation received from the user 52 and describing the performed health activity instance.

Figure 6:
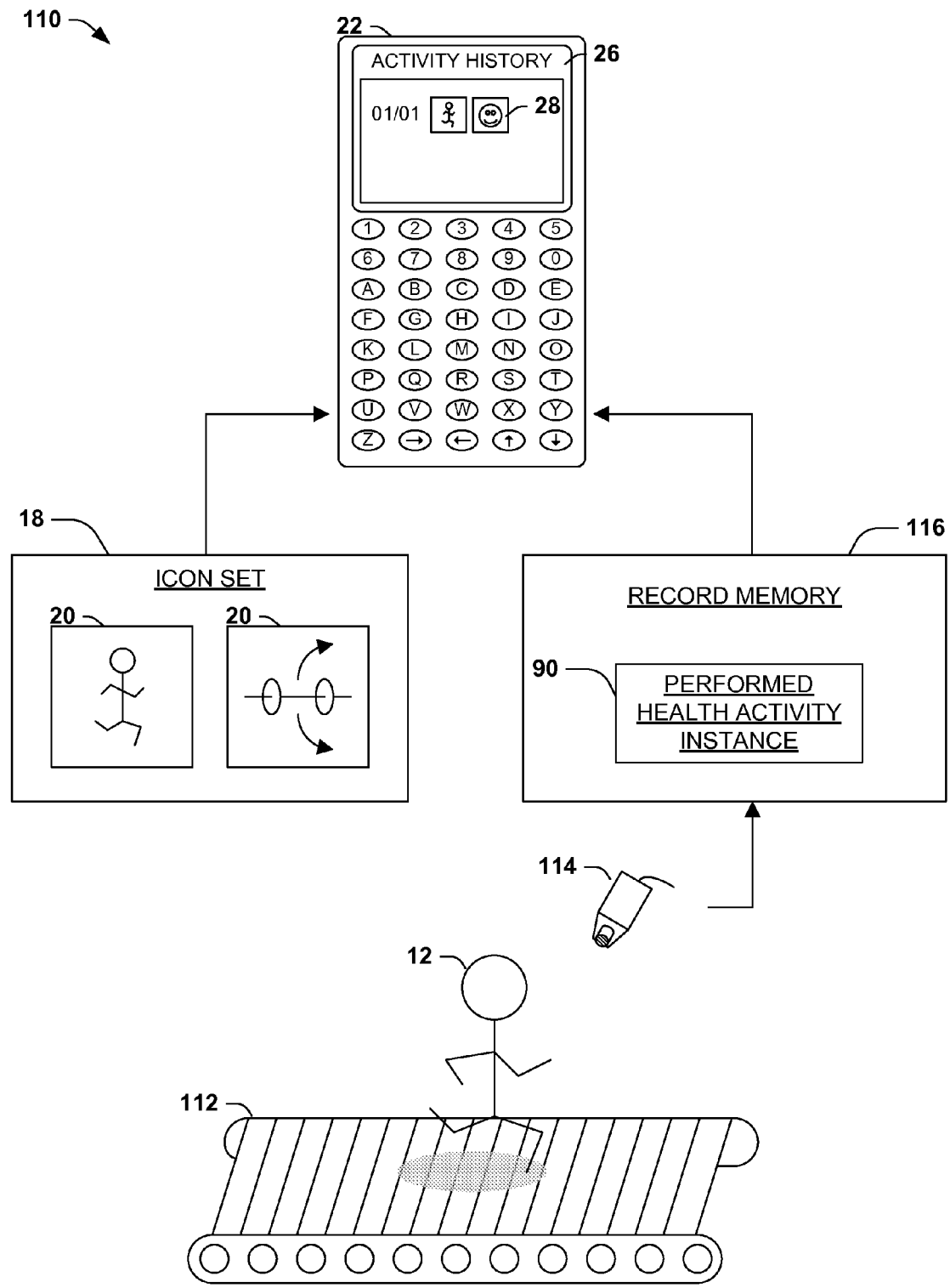
FIG. 6 illustrates an exemplary scenario featuring an embodiment configured to detect a performed health activity.

FIG. 6 presents another example, illustrated in an exemplary scenario 110 wherein the input component comprises a camera 114 configured to detect a performed health activity of an individual 12 using exercise equipment 112. In this exemplary scenario 110, the exercise equipment 112 comprises a treadmill whereupon the individual 12 may perform a running exercise. The camera 114 may be configured to detect the performance of the health activity by the individual 12, such as by evaluating the video input to detect a running motion. The camera 114 might also be configured to identify the individual 12, e.g., through a face-matching algorithm configured to compare a face detected in the video to a face database, which may be advantageous in scenarios where the exercise equipment 112 may be utilized by many individuals 12. The performed health activity detected by the camera 114 may be stored as a record in a record memory 116, which may be presented to the individual 12 (or any other user who may access the record memory 116 of the individual 12) on a device 22 as part of the activity history 26 of the individual 12. Moreover, as discussed herein, this record may be presented to the user via icons 20 stored in an icon set 18 that depict the performed health activity represented in the record. Those of ordinary skill in the art may devise many ways of recording the performed health activity instances while implementing the techniques discussed herein.

A fourth aspect that may vary among embodiments of these techniques relates to a configuration of the embodiment as a reminder device, e.g., as a device capable of generating notifications for the user of health activity instances to be performed. For example, an embodiment may be configured to, before an imminent prescribed health activity instance, notify the user 52 and/or the individual 12 by presenting on the display component 54 an icon 20 selected from the icon store 18 and depicting the health activity type of the imminent prescribed health activity instance (such as illustrated in FIG. 1.) This presentation may be augmented by other notification techniques, e.g., a vibration or audio device that generates a tactile or audible alarm, or a communications device configured to send email or another form of electronic message to the individual 12 and/or user 52.

A fifth aspect that may vary among embodiments of these techniques relates to the displaying of the health activity plan 14, including the performed health activity instances that are depicted using icons 20. As a first variation, if the health activities are prescribed for the individual 12 in relation to a particular health condition (e.g., an injury such as a muscle strain or tear that results in a prescription of a physical therapy regimen), the health condition may be presented (e.g., on the display component 56) along with the performed health activities relating thereto. For example, if the icon store comprises at least one health condition icon depicting the at least one health condition, then the presenting may, for respective health conditions, include a health condition icon selected from the icon store and depicting the health condition, and may present with the health condition icon the performed health activity instances prescribed in relation to the health condition. As a second variation, if an embodiment stores in the memory 60 one or more performed health activity instance descriptors, then when the health activity instance is presented on a display component 56, one or more performed health activity instance descriptors may be presented in correlation with the respective icon 20 to further describe the performed health activity instance. As a third variation, an embodiment may be capable of presenting to the user 52 a representation of future prescribed health activity instances, e.g., a calendar of upcoming health activity instances to be performed by the individual 12 (such as illustrated in FIG. 1.) For example, upon receiving from the user 52 a request to present future prescribed health activity instances, an embodiment of these techniques may present on the display component 56, for respective future prescribed health activity instances, an icon 20 selected from the icon store 18 and depicting the health activity type of the future prescribed health activity instance. Those of ordinary skill in the art may devise many presentations of the health activity plan 14 and associated information while implementing the techniques discussed herein.

A sixth aspect that may vary among embodiments of these techniques relates to additional capabilities that may be incorporated in embodiments of these techniques, and that may relate to the tracking of the performed health activity instances and the presentation thereof. As a first variation, an embodiment may be configured to compute a health activity plan compliance rating of the individual 12 based on correlations of the prescribed health activity instances to the performed health activity instances. The device may therefore display, along with the presented icons 20, a compliance rating indicator representing the health activity plan compliance rating. For example, the user may receive an "A" grade for fulfilling many of the prescribed health activities with high proficiency; a "B" grade for fulfilling many of the prescribed health activities with modest proficiency; and a "C" grade for fulfilling only some of the prescribed health activities. As a second variation, an embodiment may be configured to compute a proficiency trend among performed health activity instances of a health activity type (e.g., whether the individual 12 is improving in the performance of a particular health activity, such as increasing flexibility achieved through a particular stretching exercise, or whether the individual 12 is not making progress.) The embodiment may therefore present on the display component 56 a proficiency trend indicator representing the proficiency trend among performed health activity instances of the health activity type (e.g., an upward arrow indicating an improving trend, a horizontal arrow indicating a lack of progress, or a downward arrow indicating a declining trend.) As a third variation, if the health activity plan relates to at least one health condition (e.g., a muscle strain or tear prompting the prescription of a physical therapy regimen), an embodiment may be configured to correlate performed health activity instances with at least one health condition for which the performed health activity instance was prescribed, and to compute a health condition rating of the health condition based on the correlated performed health activity instances (e.g., an indication of whether the health condition of the individual 12 is improving or worsening, based on the performance of the health activities.) The presenting may therefore include a presentation of a health condition rating indicator representing the health condition rating of the health condition. As a fourth variation, where the health activities are prescribed for the individual 12 by a healthcare provider, an embodiment may be configured to, upon receiving the notification of a performed health activity instance, send the notification to the healthcare provider, e.g., as a record of the compliance of the individual 12 with the health activity plan 14. This sending may be achieved, e.g., through the inclusion of a network device that may send an email or other electronic message over a network to the healthcare provider or a health information system utilized thereby. Those of ordinary skill in the art may devise many additional features that may be included in embodiments of these techniques.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Figure 7:
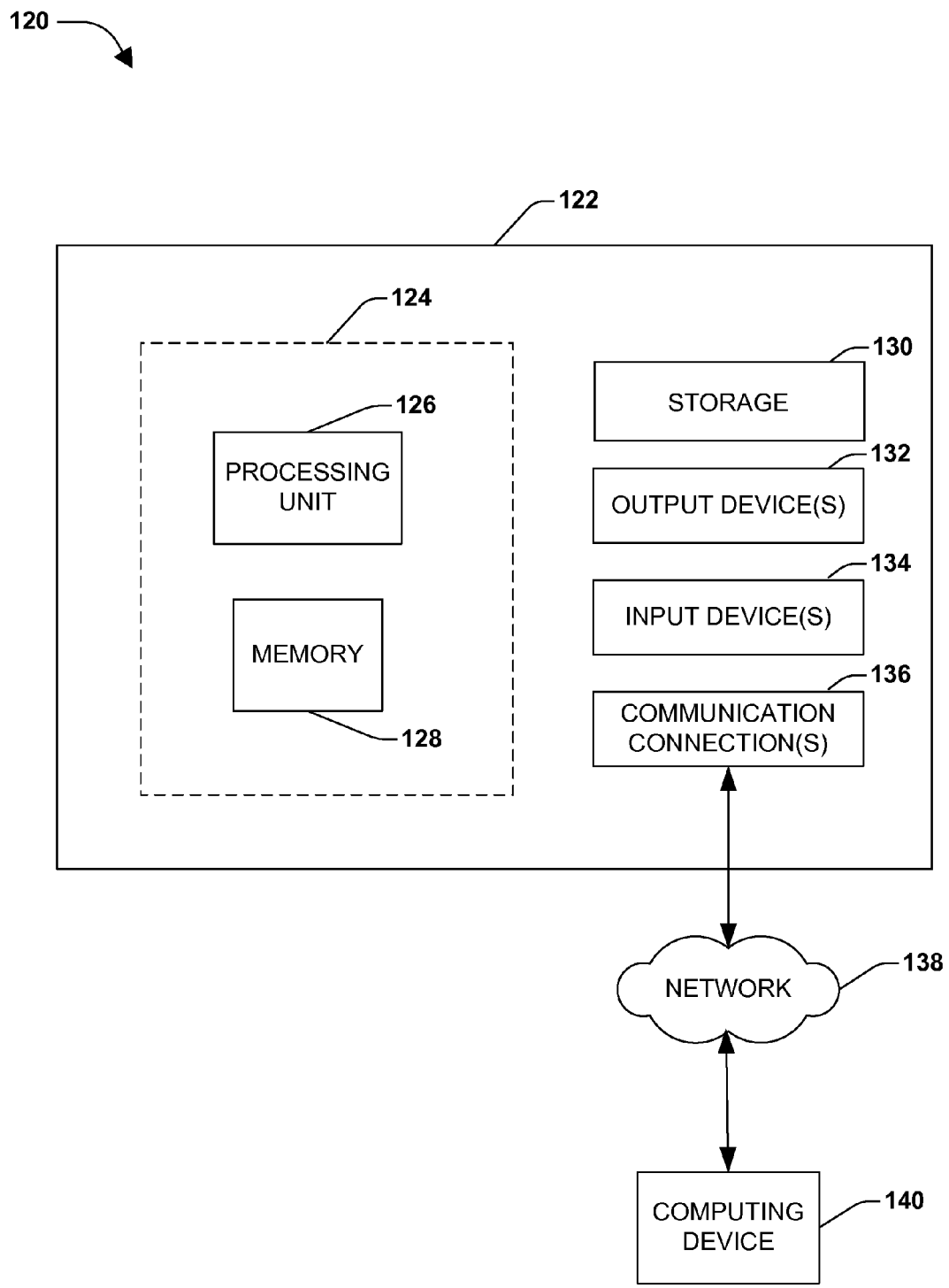
FIG. 7 illustrates an exemplary computing environment wherein one or more of the provisions set forth herein may be implemented.

FIG. 7 and the following discussion provide a brief, general description of a suitable computing environment to implement embodiments of one or more of the provisions set forth herein. The operating environment of FIG. 7 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 7 illustrates an example of a system 120 comprising a computing device 122 configured to implement one or more embodiments provided herein. In one configuration, computing device 122 includes at least one processing unit 126 and memory 128. Depending on the exact configuration and type of computing device, memory 128 may be volatile (such as RAM, for example), non-volatile (such as ROM, flash memory, etc., for example) or some combination of the two. This configuration is illustrated in FIG. 7 by dashed line 124.

In other embodiments, device 122 may include additional features and/or functionality. For example, device 122 may also include additional storage (e.g., removable and/or non-removable) including, but not limited to, magnetic storage, optical storage, and the like. Such additional storage is illustrated in FIG. 7 by storage 130. In one embodiment, computer readable instructions to implement one or more embodiments provided herein may be in storage 130. Storage 130 may also store other computer readable instructions to implement an operating system, an application program, and the like. Computer readable instructions may be loaded in memory 128 for execution by processing unit 126, for example.

The term "computer readable media" as used herein includes computer storage media. Computer storage media includes volatile and nonvolatile, removable and non-removable media implemented in any method or technology for storage of information such as computer readable instructions or other data. Memory 128 and storage 130 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 122. Any such computer storage media may be part of device 122.

Device 122 may also include communication connection(s) 136 that allows device 122 to communicate with other devices. Communication connection(s) 136 may include, but is not limited to, a modem, a Network Interface Card (NIC), an integrated network interface, a radio frequency transmitter/receiver, an infrared port, a USB connection, or other interfaces for connecting computing device 122 to other computing devices. Communication connection(s) 136 may include a wired connection or a wireless connection. Communication connection(s) 136 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 122 may include input device(s) 134 such as keyboard, mouse, pen, voice input device, touch input device, infrared cameras, video input devices, and/or any other input device. Output device(s) 132 such as one or more displays, speakers, printers, and/or any other output device may also be included in device 122. Input device(s) 134 and output device(s) 132 may be connected to device 122 via a wired connection, wireless connection, or any combination thereof. In one embodiment, an input device or an output device from another computing device may be used as input device(s) 134 or output device(s) 132 for computing device 122.

Components of computing device 122 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 122 may be interconnected by a network. For example, memory 128 may be comprised of multiple physical memory units located in different physical locations interconnected by a network.

Those skilled in the art will realize that storage devices utilized to store computer readable instructions may be distributed across a network. For example, a computing device 140 accessible via network 138 may store computer readable instructions to implement one or more embodiments provided herein. Computing device 122 may access computing device 140 and download a part or all of the computer readable instructions for execution. Alternatively, computing device 122 may download pieces of the computer readable instructions, as needed, or some instructions may be executed at computing device 122 and some at computing device 140.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "exemplary" is used herein to mean serving as an example, instance, or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method of tracking health activities prescribed for an individual on a computer accessible to a user and having a processor, a memory, at least one input component, at least one display, and an icon store configured to store health activity icons depicting health activity types, the method comprising:
executing on the processor instructions configured to:
store in the memory a health activity plan comprising at least one prescribed health activity instance of a prescribed health activity type;
upon receiving from at least one input component an at least partial recording of an activity of a person:
store the at least partial recording of the activity of the person,
using the at least partial recording of the activity of the person, identify a performed health activity instance of a performed health activity type relating to the individual, and
store in the memory a performed health activity record representing the performed health activity instance of the performed health activity type relating to the individual; and
upon receiving from the user a request to present the performed health activity instances, present on the display component, for respective performed health activity records:
an icon selected from the icon store depicting the performed health activity type,
an at least partial recording of at least one activity of a person associated with a health activity instance, and
an indicator of at least one prescribed health activity instance correlating to the performed health activity instance.

2. The method of claim 1:
the instructions further configured to receive the health activity plan by displaying for the user icons selected from the icon store and depicting health activity types that may be prescribed for the individual; and
storing the health activity plan comprising: upon receiving a selection by the user of at least one icon, storing in the memory a prescribed health activity instance of the health activity type represented by the selected icon.

3. The method of claim 1, the input component configured to receive the notification of the performed health activity instance from the user.

4. The method of claim 3, wherein the identifying the performed health activity instances using the at least partial recording comprises:
displaying for the user the at least partial recording of the activity of the person;
displaying for the user at least one icon selected from the icon store and depicting the health activities that may be performed by the individual, and
receiving from the user a selection of at least one icon.

5. The method of claim 1, the performed health activity record further comprising at least one performed health activity instance descriptor selected from a set of health activity instance descriptors comprising:
the performed health activity type;
the time of the performed health activity instance;
a proficiency of the performed health activity instance;
an annotation received from the user and describing the preformed health activity instance.

6. The method of claim 5, the presenting further comprising:
for respective health activity records, presenting on the display component the at least one performed health activity instance descriptor.

7. The method of claim 1, wherein the health activity plan further comprises:
prescribed health activity instances to be performed by a person on a prescribed date;
the instructions further configured to compute a health activity plan compliance rating based on correlations of the prescribed dates of prescribed health activity instances with dates of the performed health activity instances, and
the presenting further comprising: presenting on the display component a compliance rating indicator representing the health activity plan compliance rating.

8. The method of claim 1:
the instructions further configured to compute a proficiency trend among performed health activity instances of a health activity type; and
the presenting further comprising: presenting on the display component a proficiency trend indicator representing the proficiency trend among performed health activity instances of the health activity type.

9. The method of claim 1, wherein the health activity plan further comprises:
at least one health activity instance of a health activity type prescribed in relation to a health condition of the individual, and
the memory further configured to store at least one health condition record representing a health condition of the individual.

10. The method of claim 9:
the icon store comprising at least one health condition icon depicting the at least one health condition, and
the presenting further comprising, for respective health conditions:
presenting on the display component a health condition icon selected from the icon store and depicting the health condition, and
presenting on the display component with the health condition icon the performed health activity instances prescribed in relation to the health condition.

11. The method of claim 9, wherein the instructions are further configured to:
correlate respective performed health activity instances with at least one
health condition for which the performed health activity instance was prescribed, and
compute a health condition rating of the health condition based on the correlated performed health activity instances; and
the presenting further comprising: for respective health conditions, presenting on the display component a health condition rating indicator representing the health condition rating of the health condition.

12. The method of claim 9, wherein the health activities are prescribed for the individual by a healthcare provider, and
the instructions further configured to, upon receiving the notification of a
performed health activity instance, send the notification to the healthcare provider.

13. The method of claim 1, the instructions further configured to, upon receiving from the user a request to present future prescribed health activity instances, present on the display component, for respective future prescribed health activity instances, an icon selected from the icon store and depicting the health activity type of the future prescribed health activity instance.

14. The method of claim 1, the instructions further configured to, before an imminent prescribed health activity instance, notify the user by presenting on the display component an icon selected from the icon store and depicting the health activity type of the imminent prescribed health activity instance.

15. A system for tracking health activities prescribed for an individual on a computer accessible to a user and having a processor, a memory, at least one input component, at least one display, the system comprising:
- an icon store configured to store health activity icons depicting health activity types;
- a health activity plan storing component configured to store in the memory a health activity plan comprising at least one prescribed health activity instance of a prescribed health activity type;
- a performed health activity instance storing component configured to, upon receiving from at least one input component an at least partial recording of an activity of a person:
  - store the at least partial recording of the activity of the person,
  - using the at least partial recording of the activity of the person, identify a performed health activity instance of a performed health activity type relating to the individual, and
  - store in the memory a performed health activity record representing the performed health activity instance of the performed health activity type relating to the individual; and
- a performed health activity instance presenting component configured to, upon receiving from the user a request to present the performed health activity instances, present on the display component, for respective performed health activity records:
  - an icon selected from the icon store depicting the performed health activity type,
    - an at least partial recording of at least one activity of a person associated with a health activity instance, and
  - an indicator of at least one prescribed health activity instance correlating to the performed health activity instance.

16. The system of claim 15, the input component further configured to identify the performed health activity instances using the at least partial recording by:
- displaying for the user the at least partial recording of the activity of the person;
- displaying for the user at least one icon selected from the icon store and depicting the health activities that may be performed by the individual, and receiving from the user a selection of at least one icon.

17. The system of claim 15, wherein the health activities are prescribed for the individual by a healthcare provider, and
the system further comprising: a communications component configured to, upon
identifying a performed health activity instance, send the notification to the healthcare provider.

18. A non-transitory computer-readable medium comprising instructions that, when executed on a processor of a computer accessible to a user and having a memory, at least one input component, at least one display, and an icon store configured to store health activity icons depicting health activity types, track health activities prescribed for an individual by:
- storing in the memory a health activity plan comprising at least one prescribed health activity instance of a prescribed health activity type;
- upon receiving from at least one input component an at least partial recording of an activity of a person:
- storing the at least partial recording of the activity of the person,
- using the at least partial recording of the activity of the person, identifying a performed health activity instance of a performed health activity type relating to the individual, and
- storing in the memory a performed health activity record representing the performed health activity instance of the performed health activity type relating to the individual; and
- upon receiving from the user a request to present the performed health activity instances, presenting on the display component, for respective performed health activity records:
- an icon selected from the icon store depicting the performed health activity type,
- an at least partial recording of at least one activity of a person associated with a health activity instance, and
- an indicator of at least one prescribed health activity instance correlating to the performed health activity instance.

* * * * *